United States Patent [19]

Weiss et al.

[11] Patent Number: 4,461,016

[45] Date of Patent: Jul. 17, 1984

[54] METHOD OF AND DEVICE FOR FORMING AN IMAGE OF A LAYER OF A THREE-DIMENSIONAL OBJECT

[75] Inventors: Hermann Weiss, Duvenstedt; Erhard Klotz, Halstenbek, both of Fed. Rep. of Germany

[73] Assignee: U.S. Philips Corporation, New York, N.Y.

[21] Appl. No.: 452,574

[22] Filed: Dec. 23, 1982

Related U.S. Application Data

[63] Continuation of Ser. No. 193,208, Oct. 2, 1980, abandoned.

[30] Foreign Application Priority Data

Oct. 3, 1979 [DE] Fed. Rep. of Germany ....... 2940005

[51] Int. Cl.³ .............................................. A61B 6/00
[52] U.S. Cl. ......................................... 378/23; 378/25
[58] Field of Search ................... 378/21, 25, 193, 23, 378/92

[56] References Cited

U.S. PATENT DOCUMENTS

| | | | |
|---|---|---|---|
| 4,078,177 | 3/1978 | Tiemens | 378/23 |
| 4,132,896 | 1/1979 | Klotz et al. | 378/23 |
| 4,232,226 | 11/1980 | Huettner et al. | 378/25 |
| 4,246,483 | 1/1981 | Weiss et al. | 378/193 |

Primary Examiner—Alfred E. Smith
Assistant Examiner—T. N. Grigsby
Attorney, Agent, or Firm—Marc D. Schechter

[57] ABSTRACT

The invention relates to a method of and a device for forming images of a layer of a three-dimensional object. In order to obtain high-quality images, the object is irradiated by means of a necessarily large number of radiation sources which are arranged in different mutually parallel planes or which are arranged to be displaceable (for example, rotatable) with respect to the object. Alternatively, the object with the record carrier (X-ray film) may be arranged to be displaceable with respect to the radiation sources. In the decoding step (superposition and summing of the shadow images) use is made of the two dimensional distribution of all radiation sources used during coding (irradiation) of the object.

12 Claims, 3 Drawing Figures

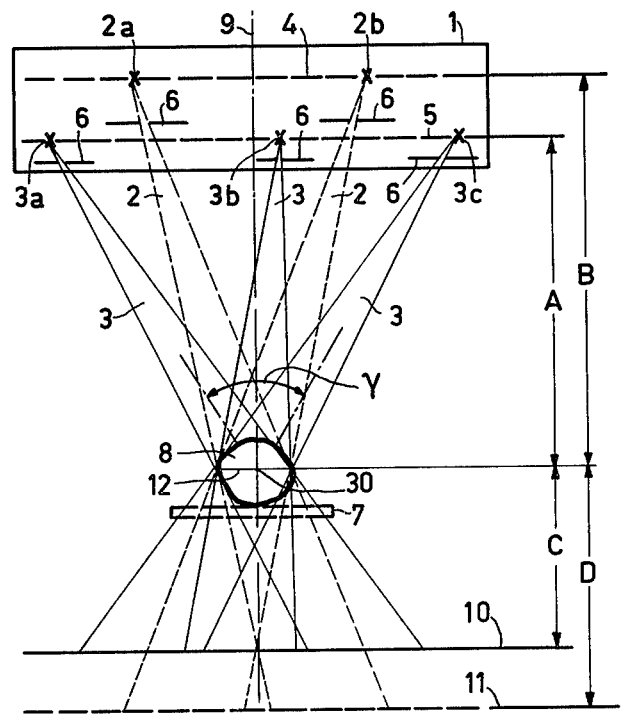

METHOD OF AND DEVICE FOR FORMING AN IMAGE OF A LAYER OF A THREE-DIMENSIONAL OBJECT

This is a continuation of application Ser. No. 193,208, filed Oct. 2, 1980 and now abandoned.

BACKGROUND OF THE INVENTION

The invention relates to a method of forming images of a layer of a three-dimensional object. The object is irradiated by a group of radiation sources (of a multiple radiation source) which are arranged in one plane. The irradiated object casts shadow images which are recorded by a radiation-sensitive layer which is situated in a recording plane. An image of a layer of the object is obtained from the shadow images by superposition and summing.

A method of this kind is already known from German Offenlegungsschrift No. 25 14 988. According to this method, the object is irradiated from a large number of radiation sources, for example, from 20 to 30 different directions (by means of a corresponding number of radiation sources), in order to record shadow images which are situated in different planes and to obtain adequate information concerning the three-dimensional object for medical diagnostic radiology. Such a large number of radiation sources, for example X-ray tubes having stationary anodes, however, cannot be accomodated within an arbitrarily small space because of the size of the radiation sources. For example, in order to prevent high-voltage flashovers in X-ray tubes, it is not possible to arrange the X-ray tubes in the closest packing which is physically possible.

Consequently, the recording angle of the radiation source distribution (i.e. the angle at which the central rays, of the radiation beams which are emitted by the radiation sources which are situated furthest from each other, intersect each other when there is a fixed distance between the plane of the radiation sources and the object) assumes comparatively high values. In tomography there are special examination methods (zonography) by means of which images can be formed of thicker object layers. However, this requires very small recording angles of, for example, 10°. Such small recording angles, however, cannot be obtained by means of known multiple radiation sources in view of the large number of radiation sources, their predetermined plot distribution and the required minimum distance therebetween. Abstaining from the use of the radiation sources which are furthest apart is not possible either, because information concerning the three-dimensional object is lost, so that the quality of the image to be realized is reduced. In order to achieve a high quality imager of a layer, it is necessary to irradiate the object with an as large as possible number of radiation sources, even when the recording angle is large.

SUMMARY OF THE INVENTION

It is an object of the invention to provide a method of forming an image of a layer of an object where the object can be irradiated at a very small as well as a very large recording angle from the number of radiation source positions, which is required for forming high-quality images of layers of an object.

The method according to the invention, where the shadow images are recorded in recording planes which are situated at different distances from the object which are parallel to the radiation source plane, and which are subsequently scaled, is characterized in that the three-dimensional object is further irradiated by radiation sources which are situated in at least one further radiation source plane which is parallel to the first radiation source plane. The group of radiation sources situated in a radiation source plane is consecutively switched on and off. The shadow images of each group of radiation sources are recorded on radiation-sensitive layers which are situated at different distances from the object, the ratio of the distances of the various radiation source planes and of the associated recording planes from the object being constant. An image of a layer of the object is the obtained by a superposition of the scaled shadow images, produced by all radiation sources used for the irradiations.

In a further method according to the invention, the object is irradiated at least twice by a number of radiation sources which are situated in one plane. Each of the radiation sources moves relative to the object after each irradiation and assumes a different position in planes which are parallel with respect to each other. The position of the radiation-sensitive layer in the recording plane remains unchanged with respect to the object. An image of a layer of the object is then obtained by super-position of the shadow images, produced by all radiation sources used.

When the number of individual radiation sources situated in a radiation source plane of a multiple radiation source is reduced by not using individual radiation sources of the distribution which are situated far from each other, the recording angle can be substantially reduced for a given distance between radiation source plane and object. If the total number of individual radiation sources is smaller than the number of radiation sources required for obtaining high-quality images, any resultant information loss concerning the three-dimensional object can be avoided by additional irradiations of the object by means of sources which are arranged in two or more mutually parallel radiation source planes. All radiation sources are then stopped down so that they irradiate substantially a common object volume.

The number of separate radiation sources, or the number of directions from which the object is irradiated, can also be increased by moving the radiation sources and the object with respect to each other. For example, the multiple radiation source can be rotated with respect to the stationary object around a central axis which extends perpendicular to the radiation source plane and through the object. The individual radiation beams intersect each other in the object and the central axis, so that almost the same object volume is irradiated in any position of the radiation sources after a rotation. The position of a record carrier for recording the shadow images then remains unchanged with respect to the object.

However, it is alternately possible to displace the object with respect to the stationary multiple radiation source in a plane parallel to the radiation source plane, for example in a straight line, while the record carrier (radiation-sensitive layer) is moved in the same way parallel with respect to the plane of the radiation source, so that the position thereof again remains unchanged with respect to the object. During displacement of the object it is only necessary to ensure that the object is irradiated in all positions by all radiation beams. This can be realized, for example, by displacing a diaphragm plate parallel to the plane of the radiation source. This plate is provided with apertures such that all radiation beams of the multiple radiation source are always stopped down to cover the object.

BRIEF DESCRIPTION OF THE DRAWING

FIG. 1 schematically shows a device for forming shadow images by means of a multiple radiation source.

FIG. 2 is a schematic plan view of the multiple radiation source.

DESCRIPTION OF THE PREFERRED EMBODIMENTS

Figure 3:
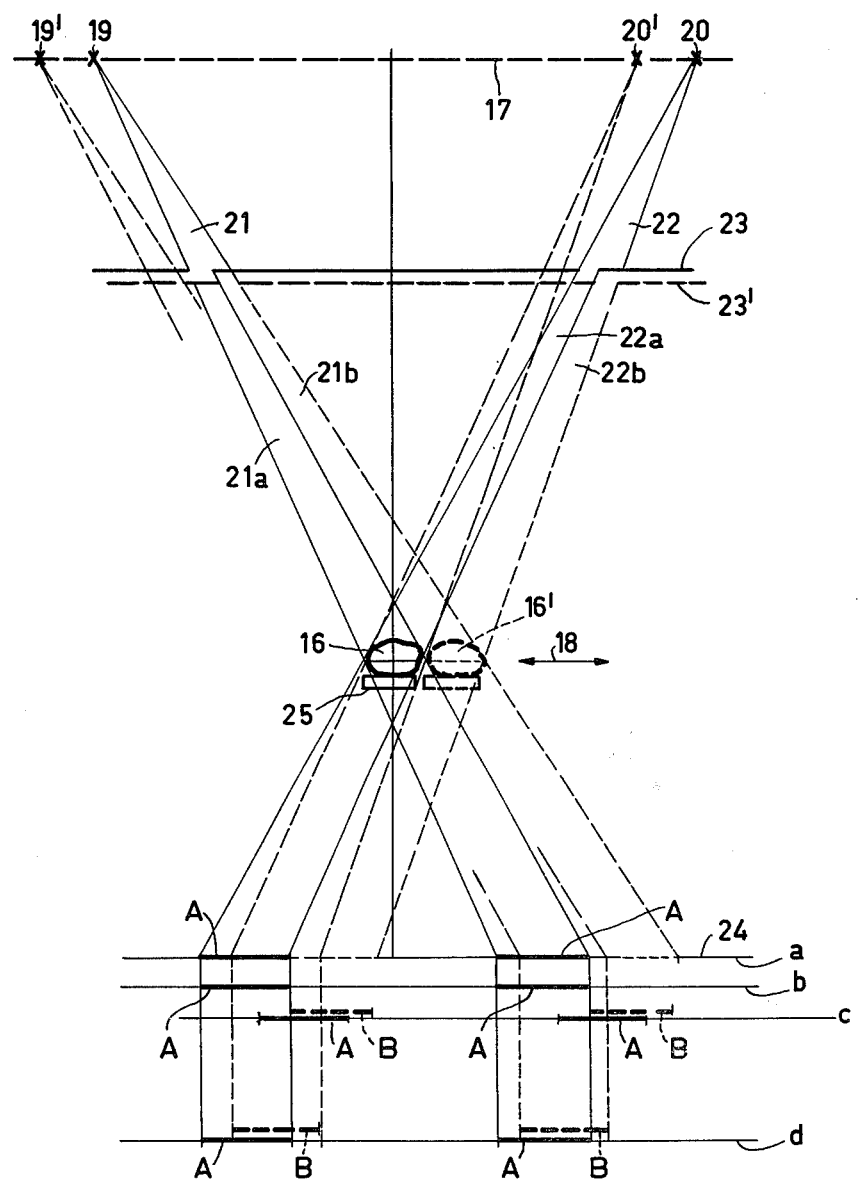
FIG. 3 schematically shows a device in which the object is displaced with respect to the stationary multiple radiation source.

FIG. 1 shows a device for forming shadow images. The device comprises a multiple radiation source 1 in which several separate X-ray tubes 2a, 2b, 3a, 3b and 3c for (example X-ray tubes having stationary anodes) are arranged in two mutually parallel radiation source planes. X-ray beams 2 and 3, generated by the X-ray tubes, pass through apertures in diaphragm 6 to irradiate an object 8 arranged on an object table 7.

The multiple radiation source 1 is, for example, an oil-filled X-ray tube tank in which the separate X-ray tubes 2a, 2b and 3a-3c are mounted without a further protective housing. The angle between the radiation beams 3, or the central rays thereof, emitted by the X-ray tubes 3a and 3c represents the recording angle $\gamma$ of the device, which is chosen to be comparatively large in this case for the sake of clarity.

The radiation beams 2 and 3 generated by the X-ray tubes arranged in the planes 4 and 5 of the radiation source are aligned so that they irradiate a common area of the object 8. The central rays of the radiation beams 2 and 3 intersect each other in a single point through which the central axis 9 of the multiple radiation source 1 also passes. The central axis extends perpendicular to the planes 4 and 5 of the radiation source. The point of intersection 30 of the central rays is situated within the object plane 12 of the object 8 shown. At the area of the point of intersection 30, rays pass through the same section of the object 8 which is situated parallel to the planes 4 and 5 of the radiation source.

The distribution of the X-ray tubes in the separate radiation source planes is preferably nonredundant. The distribution obtained by the projection of all X-ray tubes in the direction of the central rays of the radiation beams 2 and 3 on the radiation source planes 4 and 6 preferably is also nonredundant, so that images of a layer of the object which contain particularly few artefacts can be made.

The groups of X-ray tubes 2a, 2b, and 3a-3c are also connected to a generator and a control unit (not shown) by means of which the groups of X-ray tubes can be consecutively switched on and off. The multiple radiation sources, however, may also consist of a single vacuum vessel in which separate cathodes are situated opposite a common anode or opposite separate anodes. Different focusses can then be realized by the simultaneous activation of the cathodes.
T
The shadow images thus obtained are consecutively recorded on a common record carrier (radiation-sensitive layer), for example, a film. To this end, the firm or a film carrier is situated underneath the object 8 in a recording plane 10 which extends parallel to the radiation source plane 5. The film or film carrier is arranged to be displaceable in the direction of the central axis 9. In order to enable simple decoding of both groups of shadow images by means of superposition, for example, after the first irradiation by means of the separate X-ray tubes 3a-3c, the film is displaced from the recording planes 10 to the recording plane 11. After the move, the second irradiation with the X-ray tubes 2a-2b is performed. During the separate irradiations, the ratio (A/C or B/D) of the distance between the radiation source plane (4 or 5) and the object plane 12 with respect to the distance between the recording plane 10 or 11 and the object plane 12 is constant. Obviously, the groups of shadow images can also be recorded on separate X-ray films which are consecutively positioned in the recording planes 10 and 11 in a corresponding manner.

FIG. 2 is a schematic plan view of a multiple radiation source 13 which comprises four X-ray tubes 14 which are situated in one radiation source plane. The number of positions from which an object is irradiated is doubled by rotation of the multiple radiation source 13 around the central axis 90, (extending perpendicular to the radiation source plane) through a predetermined angle $\alpha$. After rotation through the angle $\alpha$, the four X-ray tubes occupy the positions 14'. For each angular position of the multiple radiation source 1, all X-ray tubes 14 are simultaneously flashed. The various groups of shadow images can then be recorded each time on separate films or on a common film. The X-ray tubes 14 are preferably arranged so that when the multiple radiation source 13 is rotated through the angle $\alpha$, the radiation source distribution composed of the rotated and the original nonredundant radiation source distribution is again nonredundant. Obviously, the X-ray tubes can also be arranged in other suitable radiation source distributions in the relevant radiation source planes.

The multiple radiation source can also be moved along arbitrary paths situated within the radiation source plane, for example, elliptical paths. The movement may be, for example, continuous with all radiation sources being flashed at given points on their paths. The corresponding groups of shadow images can then be recorded on a separate film.

For the irradiation of an object from a large number of different directions, the object can be rotated instead of rotating the radiation sources or the multiple radiation source. To this end, the object table is arranged to be rotatable, the axis of rotation coinciding with the central axis 9 of the multiple radiation source 13. The groups of shadow images obtained in various positions of the object with respect to the multiple radiation source 13 are then recorded, for example, on a separate film which is situated in accordance with the orientation of the object table or the object. In medical diagnostic radiology, a recording technique of this kind is not always possible, but it is so in the field of material testing where mainly nonliving and hence immobile objects are dealt with.

Obviously, the multiple radiation source shown in FIG. 1 with different radiation source planes can also be rotated around its central axis 9 in order to increase the number of radiation source positions. The radiation source distributions resulting from the rotation preferably are again nonredundant.

FIG. 3 shows a device for the recording of shadow images where an object 16 is displaced parallel to the radiation source plane 17 and, for example, in a straight line (arrow 18). By means of this device, the object 16 can be irradiated in a first recording step by means of the X-ray tubes 19 and 20. The radiation beams 21 and 22 of the X-ray tubes 19 and 20 are stopped down (to produce radiation beams 21a and 22a) by means of a diaphragm plate 23, which has apertures, such that the beams irradiate only the object 16 to be examined. The corresponding shadow images A are recorded on a film 24 (postion a) or on another suitable record carrier. The shadow images A on the film 24 are shown again on the line b for the sake of clarity.

During the subsequent recording step, the object 16 is displaced parallel to the radiation source plane 17 in a straight line, for example, over the object width. (The new location of the object 16' is denoted by broken lines.) This can be simply realized by displacement of the patient examination table 25 on which the object 16 is arranged. The film 24 is displaced simultneously with the examination table 25, i.e. in the same direction as the object 16 and over the same distance. To this end, the film 24 or the cassette accomodating the film, for example, is mechanically coupled to the examination table. As a result of translatory displacement of the diaphragm plate 23 (the new position is denoted by the broken line 23') parallel to the radiation source plane, the radiation beams 21 and 22 are then stopped down (to produce beams 21b, and 22b) so that they irradiate only the object 16' in its new position.

The shadow images B thus generated are recorded on the same film 24 (on line c the shadow images A and B associated with the different positions of the object 16 are denoted by broken lines). When the film 24 is returned to its original position, the object 16 then being in its starting position again, it will be seen that the film 24 contains shadow images which have been obtained by means of the X-ray tubes 19 and 20 (images A on line d) and by means of two "ficticious" X-ray tubes 19' and 20' (images B on line d). The number of X-ray tubes is thus apparently doubled, which is particularly advantageous when the object is irradiated at small recording angles. The number of X-ray tube positions can be further increased by displacing and irradiating the object several times.

The described method is suitable, for example, for examination of parts of the human vertebral column. To this end, the X-ray tubes can be arranged in a line, the longitudinal direction of the examination table 25 on which the body is positioned then extending tranverse to the connecting line of the X-ray tubes. For the recording relevant groups of shadow images, the examination table with the X-ray film is then displaced each time tranverse to the longitudinal direction of the examination table 25 and parallel to the radiation source plane over the width of the vertebral column.

For the formation of images of a layer of the three-dimensional object, the shadow images can be decoded according to German Offenlegungsschrift No. 25 14 988. The decoding (superposition and summing of the shadow images) is preferably performed by means of lenses, the positions of which correspond to the positions of all X-ray tubes used for the recording of the shadow images. For the decoding of the shadow images obtained in FIG. 3, therefore, lenses should also be used in the positions which correspond to the positions of the "ficticious" X-ray tubes 19' and 20'.

What is claimed is:

1. A method of forming an image of a layer of a three-dimensional object comprising the steps of:
    irradiating the object with radiation produced by a first radiation source, said first radiation source comprising a group of radiation sources which are arranged in a first radiation source plane;
    irradiating the object with radiation produced by a second radiation source which is arranged in a second radiation source plane, the second radiation source plane being parallel to the first radiation source plane;
    recording shadow images, produced by irradiating the object with the first source, on a radiation-sensitive layer in a first recording plane which is parallel to the radiation source planes;
    recording shadow images, produced by irradiating the object with the second source, on a radiation-sensitive layer in a second recording plane which is parallel to the first recording plane but which is situated at a different distance from the object than the first recording plane, the ratio between the distance from the first radiation source to the object and the distance from the first recording plane to the object being equal to the ratio between the distance from the second radiation source to the object and the distance from the second recording plane to the object;
    scaling the shadow images;
    consecutively switching the first and second radiation sources on and off; and
    forming an image of the layer by superposition and summing of the recorded shadow images according to the positions of all radiation sources used to irradiate the object.

2. A method as claimed in claim 1, characterized in that the shadow images are recorded on a single radiation-sensitive layer which is displaced, after each irradiation of the object, in a direction transverse to the radiation source planes.

3. A method as claimed in claim 1, characterized in that the shadow images are recorded on separate radiation-sensitive layers, alternately arranged at the first and second recording planes, respectively.

4. A device for performing the method claimed in claim 1, comprising:
    a radiation source comprising a number of separate radiation sources for irradiating the object from different directions, a first group of radiation sources being arranged in a first radiation source plane and a second group of radiation sources being arranged in a second radiation source plane which is parallel to the first radiation source plane;
    means for separately actuating the first and second groups of radiation sources; and
    a record carrier, for recording shadow images produced by the radiation sources, arranged to be displacable in a direction transverse to the radiation source planes.

5. A method of forming an image of a layer of a three-dimensional object comprising the steps of:
    irradiating the object with radiation produced by radiation sources at a number of radiation source positions which are situated in a radiation source plane;
    recording shadow images, produced by irradiating the object with the radiation sources, on a radiation-sensitive layer which is situated in a recording plane;
    moving the radiation sources in the radiation source plane relative to the object, the position of the radiation-sensitive layer relative to the object remaining unchanged;

irradiating the object with radiation produced by at least one radiation source; and forming an image of the layer by superposition and summing of the recorded shadow images according to the positions taken by all radiation sources used to irradiate the object.

6. A method as claimed in claim 5, characterized in that the relative movement of the radiation sources with respect to the object is a predetermined angular rotation around an axis which is directed perpendicular to the radiation source plane.

7. A method as claimed in claim 6, characterized in that the shadow images obtained after each angular rotation of the radiation sources are recorded on separate radiation-sensitive layers.

8. A method as claimed in claim 5, characterized in that the relative movement of the radiation sources with respect to the object is a linear displacement of the object in a plane parallel to the radiation source plane, the object being irradiated after each movement.

9. A device for performing the method claimed in claim 8, comprising:

a number of separate radiation sources for irradiating the object from different directions, said radiation sources being arranged in one radiation source plane;

an examination table for supporting the object to be irradiated, said examination table arranged to be displacable in a plane parallel to the radiation source plane;

a record carrier, for recording shadow images produced by the radiation sources, arranged to be displacable in a plane parallel to the radiation source plane; and a diaphragm device for stopping down the radiation beams from the radiation sources, said diaphragm device being arranged to be displacable in a plane parallel to the radiation source plane.

10. A device as claimed in claim 9, characterized in that the examination has a longitudinal direction and is displacable transverse to its longitudinal direction.

11. A device for performing the method claimed in claim 5, comprising:

a number of separate radiation sources for irradiating the object from different directions, said radiation sources being arranged in one radiation source plane;

an examination table for supporting the object to be irradiated; and a record carrier, for recording shadow images of the object produced by the radiation sources;

characterized in that the radiation sources are arranged to be rotatable with respect to the record carrier around a central axis which is perpendicular to the radiation source plane.

12. A device as claimed in claim 11, characterized in that the device further comprises:

means for continuously rotating the radiation sources; and means for flashing the radiation sources at given points in their rotational paths.

* * * * *